United States Patent [19]

Batina et al.

[11] Patent Number: 4,741,340
[45] Date of Patent: May 3, 1988

[54] PULSE TO SINEWAVE TELEMETRY SYSTEM

[75] Inventors: William P. Batina; Lamar H. Gipson, both of Miami, Fla.

[73] Assignee: Cordis Corporation, Miami, Fla.

[21] Appl. No.: 810,940

[22] Filed: Dec. 18, 1985

[51] Int. Cl.$^4$ ............................................. A61N 1/36
[52] U.S. Cl. .............................. 128/419 PT; 128/903
[58] Field of Search .................. 128/419 PG, 419 PT, 128/903

[56] References Cited

U.S. PATENT DOCUMENTS

| | | | |
|---|---|---|---|
| 3,650,276 | 3/1972 | Burghele et al. | 128/419 F |
| 4,220,156 | 9/1980 | Schulman et al. | 128/903 |
| 4,223,679 | 9/1980 | Schulman et al. | 128/419 PT |
| 4,281,664 | 8/1981 | Duggan | 128/419 PT |
| 4,361,153 | 11/1982 | Slocum et al. | 128/419 PT |
| 4,453,162 | 6/1984 | Money et al. | 128/903 |
| 4,528,987 | 7/1985 | Slocum | 128/903 |
| 4,550,731 | 11/1985 | Batina et al. | 128/419 PT |

*Primary Examiner*—William E. Kamm
*Attorney, Agent, or Firm*—George H. Gerstman

[57] ABSTRACT

A telemetry system for communicating with a tank circuit contained in a pacer implanted in a patient includes a telemetry coil and a capacitor connected to the telemetry coil for forming a resonant tank. The telemetry coil is positionable externally on the patient's skin substantially overlying the implanted pacer. The resonant tank has a varying impedance in response to telemetered digital data signals from the implanted tank circuit. A clock oscillator generates a squarewave at a selected frequency. A delayed clock-to-pulse converter is responsive to the squarewave for generating drive pulses which are slightly delayed from the leading edges of the squarewave. A coil driver generates a sinusoidal carrier waveform having a varying amplitude and frequency in response to the drive pulses and to the varying impedance of the resonant tank. A sample and hold circuit is provided for sampling each cycle of the sinusoidal carrier waveform of the varying amplitude and frequency to provide a sample and hold signal. An output circuit is coupled to the sample and hold circuit for recovering of the telemetered digital data signal in the form of a binary pulse-width modulated signal.

20 Claims, 7 Drawing Sheets

PULSE TO SINEWAVE TELEMETRY SYSTEM

This application is related to U.S. application Ser. No. 806,483, filed Dec. 9, 1985, in the names of William P. Batina and Lamar H. Gipson, and assigned to the assignee of the instant application.

BACKGROUND OF THE INVENTION

This invention relates generally to telemetry systems for physiological implants and more particularly, it relates to a telemetry system for communicating with an implanted cardiac pacer which samples each cycle of a sinusiodal carrier waveform from a telemetry tank for recovering telemetered digital data from the pacer.

Heretofore, there has been proposed in the prior art various telemetry systems for transmitting data into an implanted cardiac pacer as well as systems for signalling out data from the implanted pacer. However, these prior art systems relied upon the use of telemetered data which was required to be in the form of an analog message. As a result, these prior art telemetry systems have a relatively slow telemetry reception rate from the pacer which was generally limited to under 1k baud.

It would therefore be desirable to provide an improved telemetry system for recovering digital data from an implanted pacer at data rates in excess of 1k baud. The telemetry system of the present invention utilizes a sample and hold circuit for sampling each cycle of a sinusoidal carrier waveform from a telemetry tank. Since the electromagnetic field in the telemetry tank is changed in amplitude and frequency due to the loading and unloading of an implanted tank in the pacer, telemetered digital data from the pacer may be recovered by sampling of the carrier waveform as affected by the implanted tank.

SUMMARY OF THE INVENTION

Accordingly, it is a general object of the present invention to provide an improved telemetry system for communicating with an implanted cardiac pacer which is relatively simple and economical to manufacture and assemble.

It is an object of the present invention to provide a telemetry system for receiving digital data from an implanted pacer at data rates in excess of 1k baud.

It is another object of the present invention to provide a telemetry system for communicating with a tank circuit contained in a pacer implanted in a patient which includes a sample and hold circuit for sampling of each cycle of a sinusoidal carrier waveform generated from a telemetry tank.

It is still another object of the present invention to provide a system for detecting proximity of an external programming and telemetry unit with respect to an implanted pacer which includes an acquisition circuit responsive to a sample and hold signal to generate a pulse drain having a varying frequency which increases as the distance of a telemetry coil to the implanted pacer decreases.

In accordance with these aims and objectives, the present invention is concerned with the provision of a telemetry system for communicating with a tank circuit contained in a pacer implanted in a patient which includes a telemetry coil and a capacitor connected to the telemetry coil forming a resonant tank. The telemetry coil is positionable externally on the patient's skin substantially overlying the implanted pacer. The resonant tank has a varying impedance in response to telemetered digital data signals from the implanted tank circuit. A clock oscillator generates a squarewave at a selected frequency. A delayed clock-to-pulse converter is responsive to the squarewave for generating drive pulses which are slightly delayed from the leading edges of the squarewave. A coil driver generates a sinusoidal carrier waveform having a varying amplitude and frequency in response to the drive pulses and to the varying impedance of the resonant tank. A sample and hold circuit is used to sample each cycle of the sinusoidal carrier waveform of varying amplitude and frequency to provide a sample and hold signal. An output circuit is coupled to the sample and hold circuit for recovering of the telemetered digital data signals in the form of a binary pulse-width modulated signal.

BRIEF DESCRIPTION OF THE DRAWINGS

These and other objects and advantages of the present invention will become more fully apparent from the following detailed description when read in conjunction with the accompanying drawings with like reference numerals indicating corresponding parts throughout, wherein.

DESCRIPTION OF THE PREFERRED EMBODIMENTS

Figure 1:
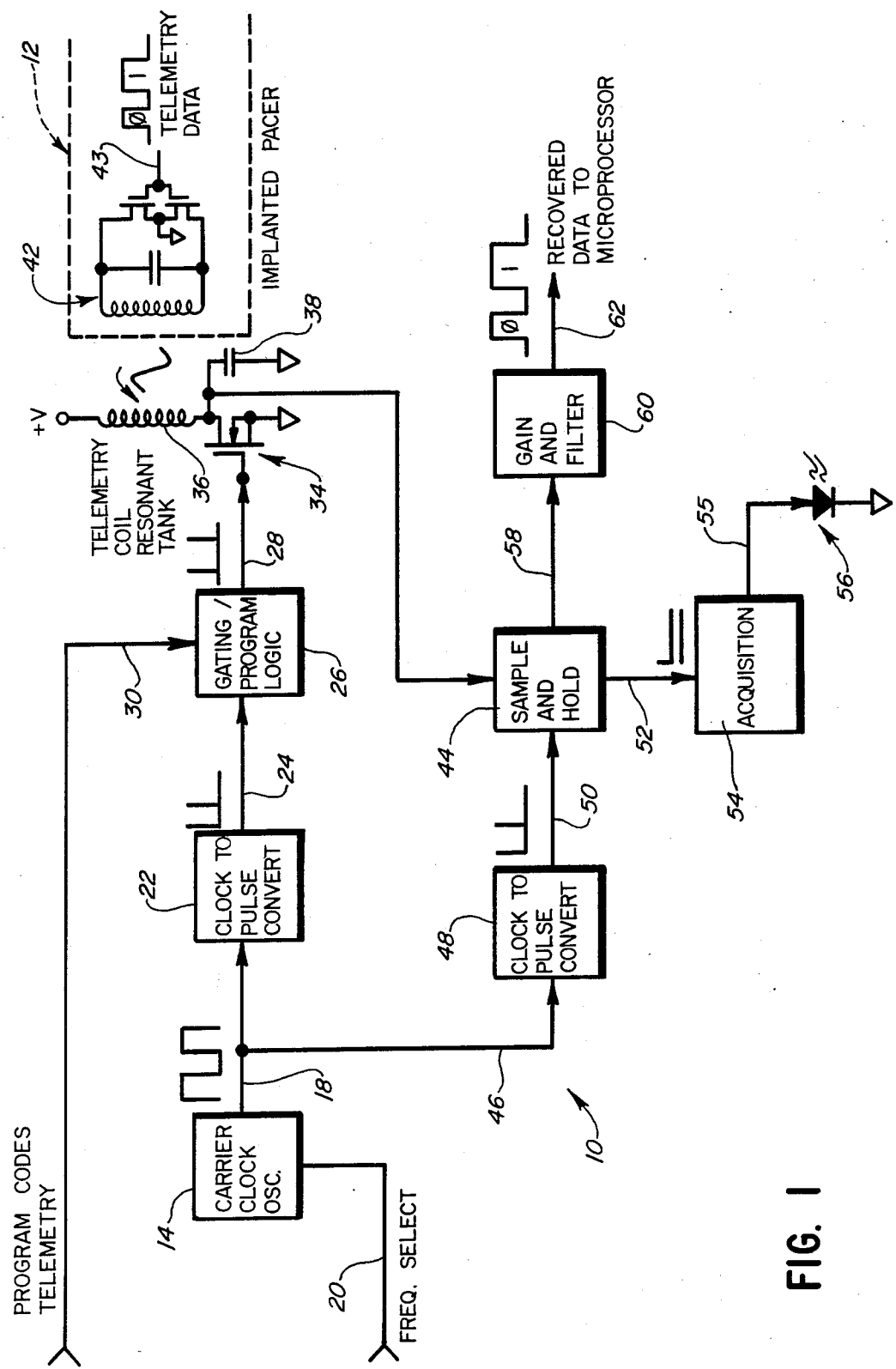
FIG. 1 is a block diagram of a telemetry system for programming an implanted pacer and/or receiving telemetered digital data from the pacer, constructed in accordance with the present invention.
Figure 3:
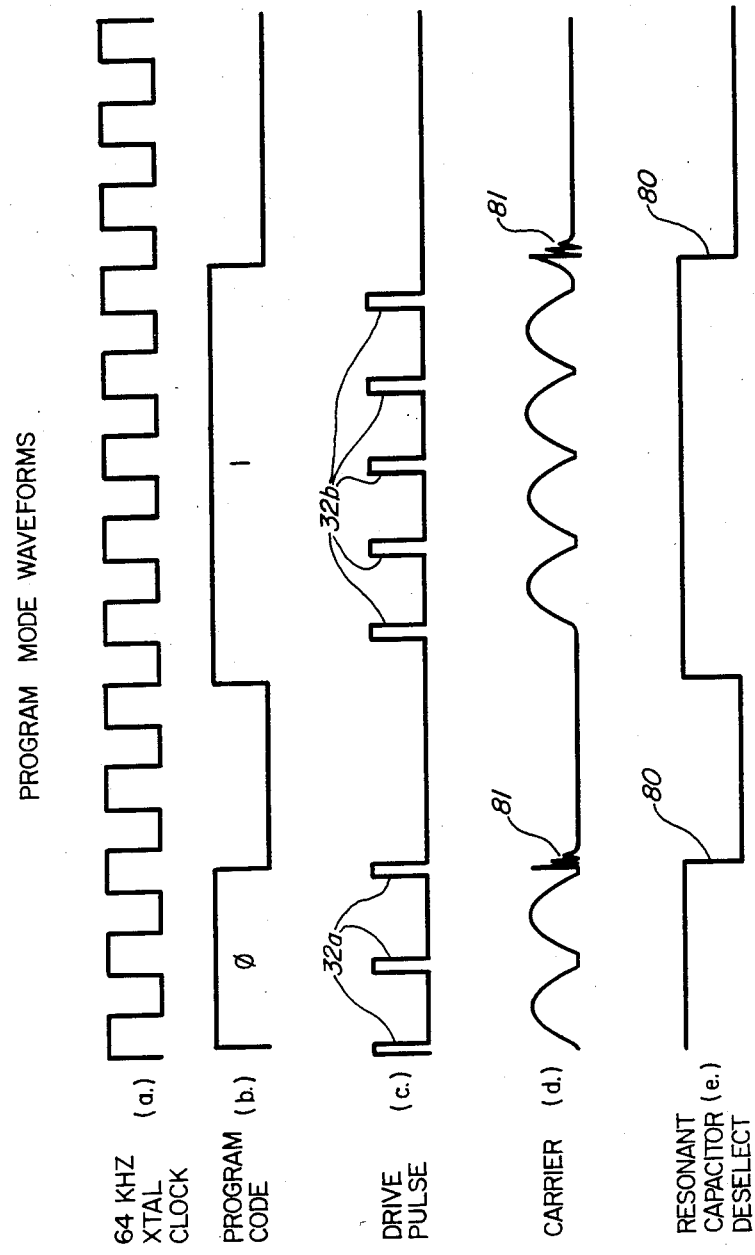
FIGS. 3, lines (a)–(e) are waveform diagrams useful in understanding the operation of the present invention.
Figure 4:
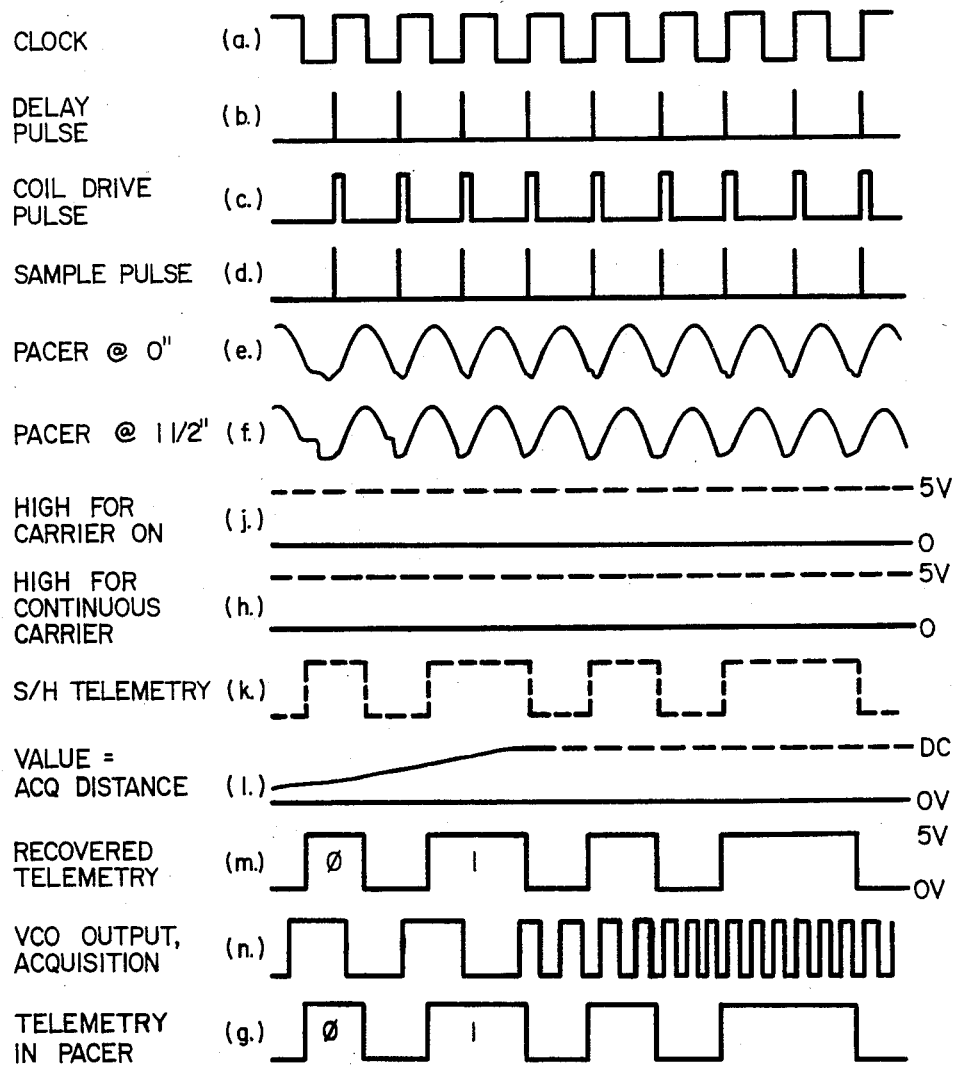
FIG. 4, lines (a)–(c) are another set of waveform diagrams useful in understanding the operation of the present invention.

Referring now in detail to the various drawings, there is shown in FIG. 1 in block diagram form a pulse-to-sinewave telemetry system of the present invention which includes an external programming and telemetry unit 10 for programming an implanted pacer 12 and/or receiving telemetered digital data or message from the pacer. The telemetry unit 10 includes a crystal-controlled carrier clock oscillator 14 which supplies squarewave pulses at 16 kilohertz or 64 kilohertz on its output on line 18. The clock oscillator 14 is responsive to a frequency select signal on line 20 for changing the oscillator frequency on the line 18 between 16 kilohertz and 64 kilohertz. The clock oscillator signal on the line 18 is shown in FIGS. 3, line (a) and 4, line (a) and is fed through a clock-to-pulse converter 22. The output of converter 22 is a series of spikes corresponding to the leading edges of the square-wave clock pulses and is depicted in FIG. 4, line (b). The output of the converter 22 on line 24 is connected to a gating/program logic circuit 26 which is operated to gate the spikes on the line 24 through to line 28 in accordance with a program code signal on line 30.

During a programming mode when digital data is being transmitted to the pacer 12, the programming code signal shown in FIG. 3, line (b) will be applied via the line 30 to the input of the gating/program logic circuit 26 so as to provide a burst of spikes forming an envelope corresponding to either "0" or "1" logic levels or states for inbound programming. The output signal of the logic circuit 26 on the line 28 during the programming mode is illustrated in FIG. 3, line (c). As can be seen, a number of spikes 32a (i.e., three) are shown which correspond to the envelope of a "0" logic level and a number of spikes 32b (i.e., five) are shown which correspond to the envelope of a "1" logic level. During a telemetry mode when digital data is being received for the pacer 12, there will be no programming code signal (i.e., it will always remain at a logic "1" level) so that the spikes will appear continuously on the output of the logic circuit 26 on the line 28 which are illustrated in FIG. 4, line (c).

The output of the logic circuit 26 is connected to the gate electrode of a field-effect transistor (FET) 34. The drain electrode of the transistor 34 is connected to one end of a telemetry coil or patient's coil 36 and to one end of a capacitor 38. The telemetry coil 36 and the capacitor 38 form a resonant tank which is tuned to the oscillator frequency for generating an electromagnetic carrier signal. The other end of the coil 12 is connected to a power supply voltage or potential +V. The source electrode of the transistor 34 and the other end of the capacitor 38 are connected to a ground potential. The drain of the transistor 34 has an output carrier signal on line 40 which is shown in FIG. 3, line (d) during the programming mode. As can be seen, during the programming mode the resonant tank changes the burst of spike (FIG. 3, line (c)) induced therein into an oscillating field or a sinewave cycle for each spike. Therefore, a carrier burst can be generated for myriametric programming of the pacer 12.

The drain of the transistor 34 has a output signal on the line 40 which are shown in FIGS. 4, line (e) and (f) during the telemetry mode. In FIG. 4 (e), the implanted pacer is substantially overlying the patient's coil. In FIG. 4, line (f), the implanted pacer 12 is approximately 1-½ inches from the patient's coil. During the telemetry mode, a continuous electromagnetic field or sinusoidal waveform is generated from the spikes (FIG. 4, line (c)) induced into the resonant tank. On a cycle-to-cycle basis, the electromagnetic energy in the resonant tank will be affected by the varying impedance in a tank circuit 42 of the implanted pacer 12. As the implanted tank circuit is loaded and unloaded in the response to a telemetered data signal which is applied to line 43 and is shown in FIG. 4, line (g), the energy in the telemetry coil 36 and the capacitor 38 will change in amplitude and frequency. This combination of amplitude and frequency changes is used to recover the digital data from the pacer 12.

The sinusoidal carrier waveform on the line 40 is connected to the input terminal of a sample and hold circuit 44. The clock pulses on the line 18 from the oscillator 14 is connected via line 46 to a clock-to-pulse converter 48 which served to generate output pulses on line 50. The leading edges of the output pulses on the line 50 coincide with the leading edges of the pulses on the line 18. These pulses on the line 50 serve as equally-spaced sample pulses which are fed to the control terminal of the sample and hold circuit 44. The sample and hold circuit 44 is used for sampling and holding (storing) the information in the sinusoidal waveform of FIG. 4, line (e) or (f).

A first output of the sample and hold circuit 44 on the line 52 is applied to an acquisition circuit 54 whose output signal on line 55 is a pulse drain having a varying frequency. This varying frequency signal will indicate proximity of the telemetry coil to the implanted pacer by increased illumination or flashing of a light-emitting diode (led) 56. In other words, the light-emitting diode 56 will flash at a higher rate as there is closer proximity of the telemetry coil to the implanted pacer.

A second output of the sample and hold circuit 44 on line 58 is fed through a gain and filter circuit block 60 which is used to square the sample and hold signal so as to form a binary pulse-width modulated signal on line 62. For example, a one millisecond (ms) pulse is a binary "0", a two ms pulse is binary "1", and the pulse-to-pulse period is three ms. This modulated signal defines the recovered digital data signal which is fed through a microprocessor (not shown) for appropriate decoding of the binary information.

Figure 2:
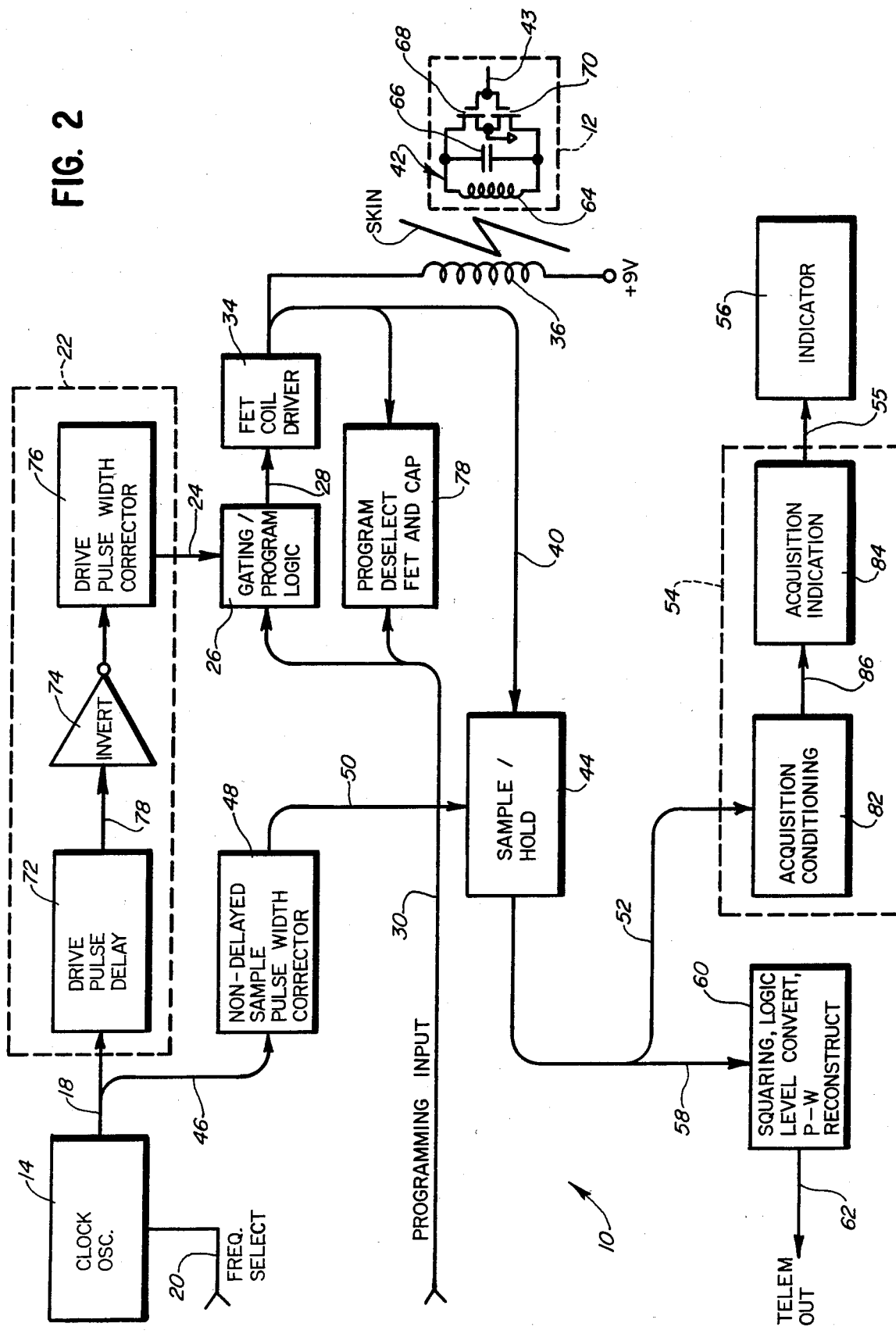
FIG. 2 is a more detailed block diagram of the telemetry system of FIG. 1.

Referring now to FIG. 2 of the drawings, there is shown a more detailed block diagram of the present external programming and telemetry unit 10 and the implanted pacer 12. The pacer 12 includes the tank circuit 42 comprised of a tuned coil 64 and a capacitor 66 and a shunt circuit for varying the impedance of the tank circuit in accordance with the telemetered digital data signal applied to the line 43. The line 43 is connected to the common gate electrodes of a pair of field-effect transistor (FET) 68 and 70. The source electrodes of the transistors 68 and 70 are connected together and to a ground potential. The drain electrodes of the transistor 68 is connected to one end of the tank circuit 42, and the drain electrode of the transistor 70 is connected to the other end of the tank circuit.

As previously discussed, the external programming and telemetry unit 10 includes the clock oscillator 14 which provides squarewave output pulses of a fixed frequency. These clock pulses on the line 18 are shown in FIG. 4, line (a) and are fed to the clock-to-pulse converter 22 consisting of a drive pulse delay circuit 72, an inverter 74 and a drive pulse width corrector circuit 76. The output of the delay circuit 72 on line 78 provides shorter pulses which are slightly delayed from the leading edges of the clock pulses. These delayed pulses from the delay circuit 72 are illustrated in FIG. 4, line (b) and are fed to the pulse-width corrector circuit 76 via the inverter 74. The corrector circuit 76 serves to increase or widen the pulse width of the delay pulses to approximately one microsecond. The output pulses of the corrector circuit 76 on the line 24 serves as drive pulses which are applied to the patient's coil 36 via the gating/program logic circuit 26 and the FET coil driver 34.

The clock pulses on the line 18 are also applied via the line 46 to the clock-to-pulse converter 48 which comprises a non-delayed sample pulse width corrector circuit. The corrector circuit 48 provides short, equally-spaced sample pulses whose leading edges coincide with the leading edges of the clock pulses. These sample pulses on the line 50 are illustrated in FIG. 4, line (d) and are fed to the sample and hold circuit 44. The programming input on the line 30 has a waveform shown in FIG. 3, line (e) which is applied to the logic circuit 26 and has a waveform shown in FIG. 3, line (d) which is applied to a program deselect circuit 78 during the programming mode. As a result, the respective pulses 32a and 32b shown in FIG. 3, line (c) form envelopes corresponding to the logic "0" state and the logic "1" state. When the programming input is not operating, the respective waveforms apply to the logic circuit 26 and the program deselect circuit 78 are in a high logic level which are depicted in FIG. 4, lines (j) and (h), respectively. Thus, the pulses on the line 28 correspond exactly to the drive pulses from the corrector 76 shown in FIG. 4, line (c). During the programming mode, each drive pulse shown in FIG. 3, line (c) generates one carrier sinewave cycle (FIG. 3, line (d)) at the output of the coil driver 34 on the line 40. The trailing edges 80 of the program deselect waveform shown in FIG. 3, line (e) are used to disconnect the capacitor 38 (FIG. 1) from the coil driver 34 so as to prevent an exponential decay at the trailing edges of the corresponding envelopes in the areas 81 in FIG. 3, line (d).

The short pulses on the line 50 are applied to the control terminal of the sample and hold circuit 44 for sampling each cycle of the sinusoidal carrier waveform (sinewave) on the line 40. While each drive pulse on the line 28 applied to the coil drive 34 generates a sinusoidal waveform of one cycle each having a predetermined amplitude and frequency, each cycle of this sinusoidal waveform is individually influenced or affected by the telemetered digital data signal on the line 43 transmitted from the pacer 12 to the telemetry coil 36. In other words, if there were no telemetry data being transmitted, each cycle of carrier waveform would be identical so long as the distance between the telemetry coil 36 and the implanted coil 64 remained the same. However, due to this influence, there is caused a loading or unloading of the resonant tank which changes its complex impedance. As a result the sinusoidal carrier waveform on the line 40 will vary in amplitude and frequency in response to the digital data applied on the line 43 and to the proximity of the external programming and telemetry unit 10 with respect to the implanted pacer. Therefore, the carrier waveform on the line 40 will represent both the proximity information and the reflected telemetry information.

Figure 5:
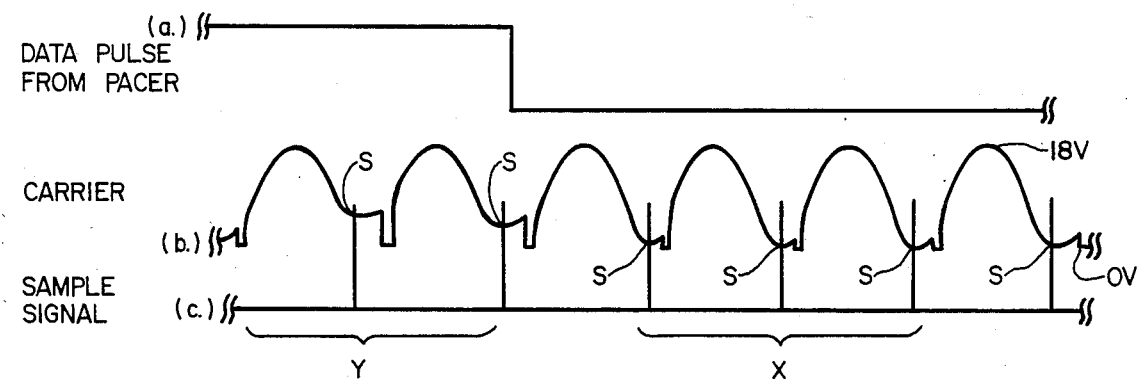
FIG. 5 (a)–5 (c) shows the manner in which the sinusoidal carrier waveform is sampled.

In FIG. 5, line (a), there is shown in an expanded form the digital data signal applied to the line 43 which consist of the binary pulse-width modulated signal. The carrier waveform on the line 40 is depicted in FIG. 5, line (b) in which each cycle thereof is varied in amplitude and frequency. The equally-spaced sampling pulses are illustrated in FIG. 5, line (c). As can be seen, at each sample point S there will be a particular voltage which is sensed. In section x of the carrier waveform in FIG. 5, line (b), there is shown a first voltage level when there is no telemetry data. In section y, there is second different voltage level at the sample points S when there is telemetry data. The sample and hold circuit 44 is used to sample and hold (stores) the voltage sensed in each cycle of the carrier waveform. Therefore, if the first voltage is sensed for a predetermined number of cycles, this are depicted in FIGS. 4 (j) and 4 (h), respectively. Thus, the pulses on the line 28 correspond exactly to the drive pulses from the corrector 76 shown in FIG. 4, line (c). During the programming mode, each drive pulse shown in FIG. 3, line (c) generates one carrier sinewave cycle (FIG. 3, line (d)) at the output of the coil driver 34 on the line 40. The trailing edges 80 of the program deselect waveform shown in FIG. 3, line (e) are used to disconnect the capacitor 38 (FIG. 1) from the coil driver 34 so as to prevent an exponential decay at the trailing edges of the corresponding envelopes in the areas 81 in FIG. 3, line (d).

The short pulses on the line 50 are applied to the control terminal of the sample and hold circuit 44 for sampling each cycle of the sinusoidal carrier waveform (sinewave) on the line 40. While each drive pulse on the line 28 applied to the coil drive 34 generates a sinusoidal waveform of one cycle each having a predetermined amplitude and frequency, each cycle of this sinusoidal waveform is individually influenced or affected by the telemetered digital data signal on the line 43 transmitted from the pacer 12 to the telemetry coil 36. In other words, if there were no telemetry data being transmitted, each cycle of carrier waveform would be identical so long as the distance between the telemetry coil 36 and the implanted coil 64 indicates that there is no telemetry data. If the second voltage is sensed for a first given number of cycles (i.e., four cycles), this indicates a logic "0" state. If the second voltage is sensed for a second given number of cycles (i.e., ten cycles), this indicates a logic "1" state. Thus, the sampled carrier waveform forming a sample and hold signal on the line 58 is illustrated in FIG. 4 (k). The sample and hold signal is delivered to the gain and filter block 60 which includes a square and logic converter formed of a squaring circuit, a logic level converter circuit, and a pulse width reconstruction circuit. From these sampled values, the telemetered digital data signals that are generated by the implanted tank circuit are reconstructed. The output of the block 60 on the line 62 is shown in FIG. 4 (m) which is the recovered telemetered digital data.

The sample and hold signal from the circuit 44 is also fed to the acquisition block 54 comprised of an acquisition conditioning circuit 82 and an acquisition indicator circuit 84. The acquisition conditioning circuit 82 provides a varying DC signal level on line 86 which is depicted in FIG. 4 (1). This DC signal is inversely proportional to the proximity of the telemetry coil to the implanted coil. The acquisition indicator circuit 84 is formed of a voltage-controlled oscillator which is responsive to the varying DC signal to generate a pulse drain having a varying frequency which increases as the distance of the telemetry coil to the implanted pacer decreases. The output signal of the acquisition indicator circuit on the line 55 is shown in FIG. 4, line (n) and is applied to the visual indicator 56 which consists of light-emitting diodes (LED).

Figure 6:
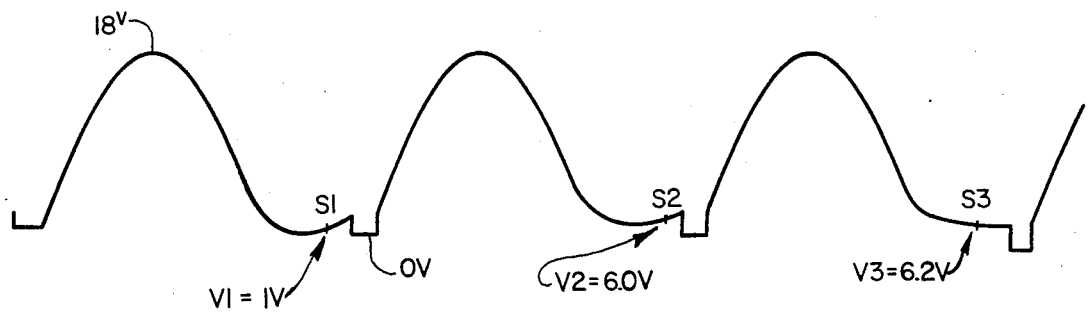
FIG. 6 illustrates how the sinusoidal carrier waveform is sampled for use with the acquisition circuit.

The manner in which the varying DC signal level is obtained will now be explained with reference to FIG. 6, which shows the carrier waveform on the line 40 during the telemetry mode. The DC level is the voltage difference between the sampled voltage and the ground potential. As the distance between the telemetry coil and the implanted coil decreases, this voltage difference and thus the DC level will be greater. At a first sample point S1 where the pacer is not in the field of the telemetry coil and no telemetry data is present, there is a sampled voltage V1 which is, for example, 1 volts. At a second sample point S2 where the pacer is in the field but there is no telemetry data, there is a sampled voltage V2 which is, for example, 6 volts. This sampled voltage V2 will be dependent upon the distance between the telemetry coil and the implanted pacer. At a third sample point S3 which is, for example, 6.2 volts, where the 0.2 volts constitutes the data. The difference between the sampled voltages V2 and V1 is the DC voltage level which is fed to the acquisition block 54.

Figure 7:
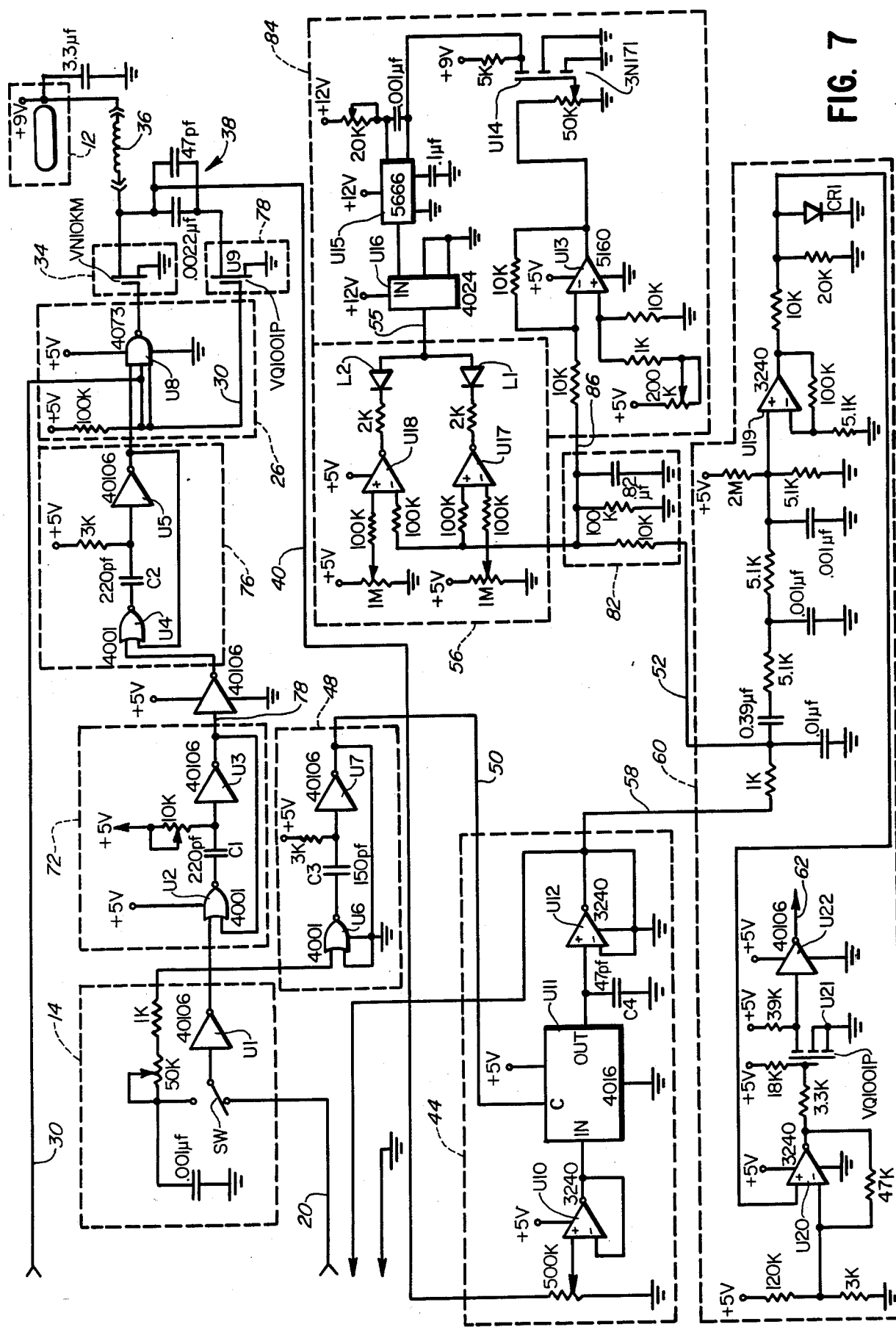
FIG. 7 is a detailed schematic circuit diagram showing circuitry suitable for use in the blocks depicted in FIG. 2.

While the various blocks in FIG. 2 may take various forms, suitable circuitry for use in the blocks thereof are illustrated in FIG. 7. Since these electronic circuits are quite conventional in nature, it is believed that the schematic diagram is self-explanatory to those skilled in the art and thus a detailed description of the operation of each circuit is believed to be unnecessary. However, it will be deemed expedient to point out that an external clock signal may be fed to the clock oscillator 14 via the line 20 from a microprocessor. When the switch SW is moved to the other position, the internal clock oscillator is used which includes a CMOS schmitt trigger U1. The delay circuit 72 comprises a one-shot multivibrator formed of a NOR logic gate U2, a capacitor C1 and a Schmitt trigger U3. The corrector circuit 76 includes a NOR logic gate U4, a capacitor C2, and a Schmitt trigger U5. The corrector circuit 48 includes a NOR logic gate U6, a capacitor C3 and a Schmitt trigger U7. The gating/program logic circuit 26 is formed of an AND gate U8, and the program deselect block 78 is formed of a field-effect transistor U9.

Further, the sample and hold circuit 44 includes an amplifier U10, a transmission gate U11, a storage capacitor C4 and an output amplifier U12. The acquisition conditioning circuit 82 comprises a series resistor (10k) and a parallel connected resistor (100k) and a capacitor (0.82 uf). The acquisition indicator circuit 84 includes a differential amplifier U13, a field-effect transistor U14, a voltage-controlled oscillator U15 and a divider U16. The visual indicator 56 includes an amplifier U17, a yellow LED L1, an amplifier U18, and a green LED L2. The gain and filter block 60 includes a low pass filter section formed of resistors and capacitors, a first non-inverting amplifier U19, a diode CR1, a second non-inverting amplifier U20, a field-effect transistor U21, and a Schmitt trigger U22.

For completeness in the disclosure of the above described telemetry system but not for purposes of limitations, the representative values and component identifications have been included in the schematic of FIG. 7. These values and components were employed in a telemetry system that was constructed and tested in which provided a high quality performance. It should be readily apparent to those skilled in the art that many alternatives elements and values may be employed in constructing the various circuits in accordance with the present invention.

Figure 8:
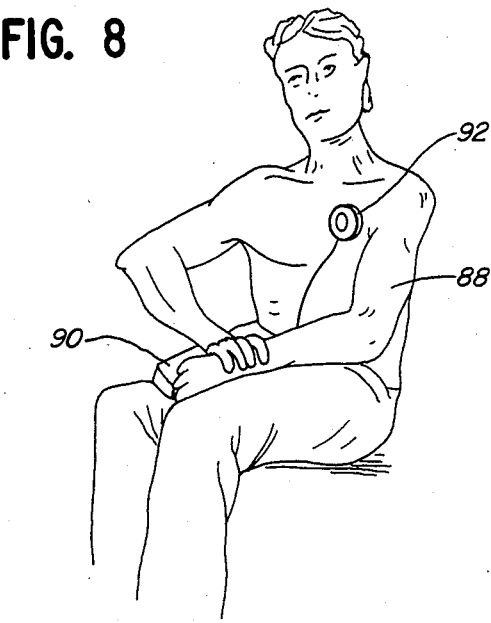
FIG. 8 illustrates a patient using the telemetry system of the present invention.
Figure 9:
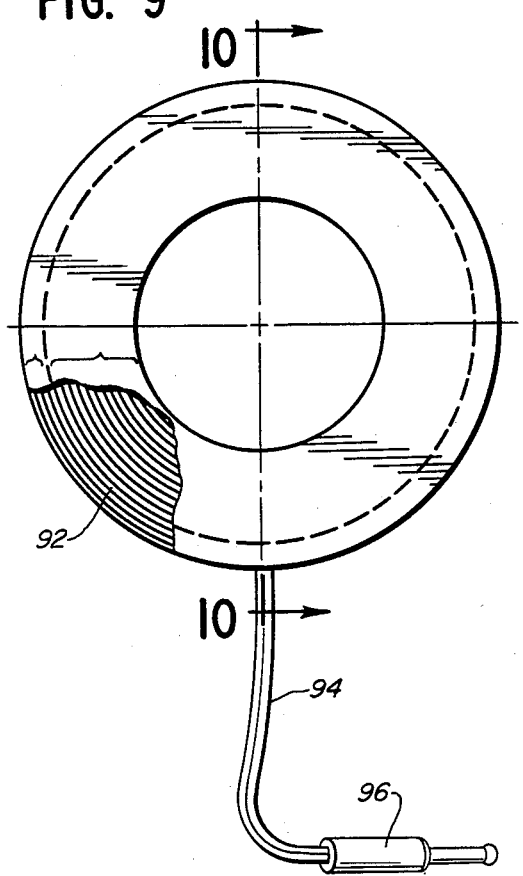
FIG. 9 is an plan, elevational view, partly broken, of an inductor coil used in connection with the present invention.

In FIG. 8, there is shown a patient 88 using the external programming and telemetry unit of the present invention which is comprised of a housing 90 and a separated inductor coil or patient's coil 92. The inductor coil 92 corresponds to the telemetry coil 36 in FIGS. 1 and 2. The inductor coil 92 is affixed to the patient's skin and is coupled to the housing 90 via a flexible electrical cord 94 and an electrical plug 96 (FIG. 9). The housing 90 contains all of the external programming and telemetry circuits of the unit 10 in the FIGS. 1 and 2, except for the telemetry coil 36 which is separated from the housing. The coil 92 comprises 160 turns of No. 28 copper wire having a central cicular opening with an diameter of approximately 1¼ inches. The coil has a generally disc-shape configuration with an outer diameter of approximately 3⅜ inches and a thickness of approximately 0.040 inches, as can best be seen in FIG. 10.

Figure 10:
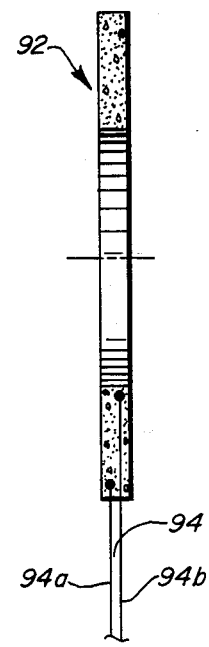
FIG. 10 is a cross-sectional view of the inductor coil, taken along the lines 10—10 of FIG. 9.
Figure 11:
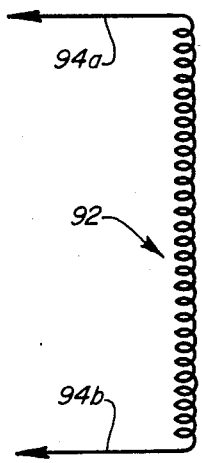
FIG. 11 is a schematic representation of the winding for the inductor coil of FIGS. 9 and 10.

Referring to FIG. 10 and 11, the ends 94a and 94b of the winding 92 form the flexible electrical cord 96. It is preferable that the winding be provided with a thermoplastic coating so that it may be heated to form a intergal unit. The coil or winding 92 is wound on a bobbin, pulled off, then encapsulated with an appropriate potting compound such as a thermosetting potting material. The coil 92 which is positionable externally on the patient's skin in proximity to or substantially overlying the implanted tank circuit is extremely lightweight and small. Further, it can be manufactured with relative ease and economy, may be made sterilizable, and may be reusable. In a preferred embodiment, both faces of the patient's coil 92 are flat so that it may be placed against the patient's skin and may be readily attached to the skin allowing the patient to wear it for a relatively long period of time. Since a sperical electromagnetic field lobe is produced with a diameter of approximately 6 inches with the above coil dimensions, this affords a significant amount of latitude with respect to obtaining signals even as the patient's coil 92 is not placed exactly over the implanted pacer.

From the foregoing detailed description, it can thus be seen that the present invention provides an improved telemetry system for communicating with an implanted cardiac pacer which samples each cycle of a sinusoidal carrier waveform generated from a telemetered tank for recovering telemetered digital data from the pacer. Further, the telemetry system of the instant invention permits the recovery of digital data from the implanted pacer at data rates in excess of 1k baud.

While there has been illustrated and described what is at present to be considered a preferred embodiment of the present invention, it will be understood by those skilled in the art that various changes and modifications may be made, and equivalents may be substituted for elements thereof without departing from the true scope of the invention. In addition, many modifications may be made to adapt a particular situation or material to the teachings of the invention without departing from the central scope thereof. Therefore, it is intended that this invention not be limited to the particular embodiment disclosed as the best mode contemplated for carrying out this invention, but that the invention will include all embodiments falling within the scope of the appended claims.

What is claimed is:

1. A telemetry system for communicating with a tank circuit contained in a pacer implanted in a patient comprising:

a telemetry coil being positionable externally on the patient's skin in proximity to the implanted pacer;

capacitive means connected to said telemetry coil for forming a resonant tank;

said resonant tank having a varying impedance in response to telemetered digital data signals from the implanted tank circuit;

clocking means for generating a squarewave at a selected frequency;

delayed clock-to-pulse converter means responsive to said squarewave for generating drive pulses which are slightly delayed from the leading edges of said squarewave;

coil driver means for generating a sinusoidal carrier waveform having a varying amplitude and frequency in response to the drive pulses and to the varying impedance of said resonant tank;

means for sampling each cycle of the sinusoidal carrier wave of varying amplitude and frequency to provide a sample and hold signal; and output means coupled to said sampling means for recovering of the telemetered digital data signals in the form of a binary pulse-width modulated signal.

2. A telemetry system as claimed in claim 1, wherein said clocking means for generating said squarewave includes a clock oscillator having a frequency of 16 kilohertz.

3. A telemetry system as claimed in claim 1, wherein said clocking means for generating said squarewave includes a clock generator having a frequency of 64 kilohertz.

4. A telemetry system as claimed in claim 1, wherein said coil driver means includes a field-effect transistor having its gate electrode coupled to said drive pulses, its drain electrode connected to said resonant tank and its source electrode connected to a ground potential.

5. A telemetry system as claimed in claim 1, wherein said sampling means includes a sample hold circuit.

6. A telemetry system as claimed in claim 1, wherein said delayed clock-to-pulse converter means includes a driver pulse delay circuit, an inverter and a drive pulse-width corrector circuit.

7. A telemetry system as claimed in claim 1, further comprising a non-delayed clock-to-pulse corrector means responsive to said squarewave for generating equally-spaced sample pulses whose leading edges coincide with the leading edge of said squarewave, said sample pulse being connected to a control terminal of said sampling means.

8. A telemetry system as claimed in claim 1, wherein said output means includes a squaring and logic level converter circuit consisting of a low pass filter and amplifier means to produce the pulse-width modulated signal.

9. A telemetry system as claimed in claim 1, further comprises acquisition means responsive to said sample and hold signal to produce a pulse train having a varying frequency which increases as the distance of the telemetry coil to the implanted pacer decreases.

10. A telemetry system as claimed in claim 9, wherein said acqustion means includes an acquisition conditioning circuit to produce a varying DC signal representative of the distance of the telemetry coil to the pacer, an acquisition indicator circuit formed of a voltage-controlled oscillator which is responsive to said DC signal to produce said pulse train of the varying frequency, and a visual indicator responsive to said pulse train which flashes at a higher rate when the telemetry coil is closer in proximity to the implanted pacer.

11. A telemetry system as claimed in claim 1, further comprising gating/program logic means responsive to a program signal for transmitting said drive pulses to the implanted tank circuit so as to program said implanted pacer.

12. A telemetry system as claimed in claim 11, further comprising program deselect means responsive to the trailing edges of said program signal for disconnecting said capacitive means so as to prevent an exponential decay in the sinusoidal carrier waveform.

13. In a telemetry system for pacing in which a pacer containing a data modulated tank circuit is implanted in a patient and a programming and telemetry unit is used external of the patient, the improvement comprising in combination:

a telemetry coil being positionable externally on the patient's skin in proximity to the implanted pacer;

capacitive means connected to said telemetry coil for forming a resonant tank;

said resonant tank having a varying impedance in response to telemetered digital data signals from the implanted tank circuit;

clocking means for generating a squarewave at a selected frequency;

delayed clock-to-pulse converter means responsive to said squarewave for generating drive pulses which are slightly delayed from the leading edges of said squarewave;

coil driver means for generating a sinusoidal carrier waveform having a varying amplitude and frequency in response to the drive pulses and to the varying impediance of said resonant tank;

means for sampling each cycle of the sinusiodal carrier wave of varying amplitude and frequency to provide a sample and hold signal; and output means coupled to said sampling means for recovering of the telemetered digital data signals in the form of a binary pulse-width modulated signal.

14. In a telemetry system as claimed in claim 13, wherein said output means includes a squaring and logic level converter circuit consisting of a low pass filter and amplifier means to produce the pulse-width modulated signal.

15. In a telemetry system as claimed in claim 13, further comprises acquisition means responsive to said sample and hold signal to produce a pulse train having a varying frequency which increases as the distance of the telemetry coil to the implanted pacer decreases.

16. A telemetry system as claimed in claim 15, wherein said acquisition means includes an acquisition conditioning circuit to produce a varying DC signal representative of the distance of the telemetry coil to the pacer, an acquisition indicator circuit formed of a voltage-controlled oscillator which is responsive to said DC signal to produce said pulse train of the varying frequency, and a visual indicator responsive to said pulse train which flashes at a higher rate when the telemetry coil is closer in proximity to the implanted pacer.

17. In a telemetry system as claimed in claim 13, further comprising gating/program logic means responsive to a program signal for transmitting said drive pulses to the implanted tank circuit so as to program said implanted pacer.

18. In a telemetry system as claimed in claim 17, further comprising program deselect means responsive to the trailing edges of said program signal for disconnecting said capacitive means so as to prevent an exponential decay in the sinusoidal carrier waveform.

19. A system for detecting proximity of an external program and telemetry unit with respect to an implanted pacer comprising:

a telemetry coil being positionable externally on the patient's skin in proximity to the implanted pacer;

capacitive means connected to said telemetry coil for forming a resonant tank;

said resonant tank having a varying impedance in response to telemetered digital data signals from the implanted tank circuit;

clocking means for generating a squarewave at a selected frequency;

delayed clock-to-pulse converter means responsive to said squarewave for generating drive pulses which are slightly delayed from the leading edges of said squarewave;

coil driver means for generating a sinusoidal carrier waveform having a varying amplitude and frequency in response to the drive pulses and to the varying impedance of said resonant tank;

means for sampling each cycle of the sinusoidal carrier wave of varying amplitude and frequency to provide a sample and hold signal; and acquisition means responsive to said sample and hold signal to produce a pulse train having a varying frequency which increases as the distance of the telemetry coil to the implanted pacer deceases.

20. A system for detecting proximity as claimed in claim 19, wherein said acquisition means includes an acquisition conditioning circuit to produce a varying DC signal representative of the distance of the telemetry coil to the implanted pacer, an acquisition indicator circuit formed of a voltage-controlled oscillator which is responsive to said DC signal to produce said pulse train of the varying frequency, and a visual indicator responsive to said pulse train which flashes at a higher rate when the telemetry coil is closer in proximity to the implanted pacer.

* * * * *